United States Patent
Berni Canani et al.

(10) Patent No.: US 9,255,062 B2
(45) Date of Patent: Feb. 9, 2016

(54) FATTY ACID DERIVATIVES FOR ORAL ADMINISTRATION ENDOWED WITH HIGH PALATABILITY

(76) Inventors: Roberto Berni Canani, Naples (IT); Antonio Calignano, Naples (IT); Orazio Mazzoni, Castellammare di Stabia (IT); Orietta Mazzoni, legal representative, Castellammare di Stabia (IT); Anna Coruzzo, Ercolano (IT)

(*) Notice: Subject to any disclaimer, the term of this patent is extended or adjusted under 35 U.S.C. 154(b) by 1135 days.

(21) Appl. No.: 12/988,556

(22) PCT Filed: Apr. 21, 2009

(86) PCT No.: PCT/IT2009/000179
§ 371 (c)(1),
(2), (4) Date: Dec. 16, 2010

(87) PCT Pub. No.: WO2009/130735
PCT Pub. Date: Oct. 29, 2009

(65) Prior Publication Data
US 2011/0098319 A1  Apr. 28, 2011

(30) Foreign Application Priority Data
Apr. 21, 2008  (IT) .............. RM2008A0214

(51) Int. Cl.
*A61K 31/40* (2006.01)
*A61K 31/44* (2006.01)
*A61K 31/165* (2006.01)
(Continued)

(52) U.S. Cl.
CPC .............. *C07C 231/02* (2013.01); *C07C 233/31* (2013.01); *C07C 233/91* (2013.01)

(58) Field of Classification Search
CPC ...... A61K 31/40; A61K 31/44; A61K 31/165
USPC .............. 548/333.5, 530; 514/399, 613, 354, 514/423; 564/123; 546/249, 314
See application file for complete search history.

(56) References Cited

U.S. PATENT DOCUMENTS

2006/0211603 A1*  9/2006  Raju ...................... C07K 9/008
514/2.9

OTHER PUBLICATIONS

Kang, S et al. "Different Acyl Specificity between Mold and Kidney Acylases . . . " Bulletin of the Chemical Society of Japan, vol. 61, (1988), pp. 575-576.*

(Continued)

*Primary Examiner* — Kamal Saeed
*Assistant Examiner* — Janet L Coppins
(74) *Attorney, Agent, or Firm* — Gregory P. Einhorn; Greer Burns & Crain Ltd.

(57) ABSTRACT

The invention relates to novel derivatives of short-chain fatty acids, in particular derivatives of butyric acid, useful for all the known clinical applications of the latter, which show physicochemical characteristics suitable for an easy oral administration, being devoid of the unpleasant organoleptic properties that characterize butyrate. The new compounds are amide derivatives which can be synthesized by reaction of the corresponding fatty acid halide with a naturally occurring amino acid, phenylalanine or a suitable derivative thereof, and which are in a poorly hygroscopic, easily weighable form, stable to acids and alkalis and able to release the acid at the small and large bowel level in a constant manner over time. They do not have disagreeable odors and are practically tasteless, thus allowing the manufacture of preparations for oral administration also suitable for the therapy of chronic diseases and in the pediatric field.

23 Claims, 1 Drawing Sheet

(51) Int. Cl.
C07D 213/127 (2006.01)
C07D 207/04 (2006.01)
C07C 15/04 (2006.01)
C07C 231/02 (2006.01)
C07C 233/31 (2006.01)
C07C 233/91 (2006.01)

(56) References Cited

OTHER PUBLICATIONS

Iselin, B. M. et al, J.Am.Chem.Society (1950), pp. 1729-1731.*
CAPLUS Accession No. 1993:6901, abstract of "Mazurkiewicz, Roman," Synthesis (1992), vol. 10, pp. 941-943.*
CAPLUS Accession No. 1978:169737, abstract of Basha et al, Tetrahedron Letters (1977), vol. 48, pp. 4171-4174.*
Berni Canani, Roberto, "Butyrate as an Effective Treatment of Congenital Chloride Diarrhea", Gastroenterology, 2004, 127:630-634.
Berni Canani, Roberto, "Effects of HIV-1 Tat Protein on Ion Secretion and on Cell Proliferation in Human Intestinal Epithelial Cells," Gastroenterology, 2003, 124:368-376.
Berni Canani, Roberto, "Zinc Inhibits Cholera Toxin-Induced, but Not Escherichia coli Heat-Stable Enterotoxin-Induced, Ion Secretion in Human Enterocytes," JID, Apr. 1, 2005, 191, 1072-1077.
Berni Canani, Roberto, "Growth hormone regulates intestinal ion transport through a modulation of the constitutive nitric oxide synthase-nitric oxide-cAMP pathway," World J. Gastroenterol, Aug. 7, 2006, vol. 12, No. 29, 4710-4715.
Biagi, G., "Performance, intestinal microflora, and wall morphology of weanling pigs fed sodium butyrate," J. Anim. Sci., 2007, 85:1184-1191.
Boffa, Lidia C., "Manifold Effects of Sodium Butyrate on Nuclear Function," The Journal of Biological Chemistry, vol. 256, No. 18, Sep. 25, 1981, pp. 9612-9621.
Breuer, R.I., "Short chain fatty acid rectal irrigation for left-sided ulcerative colitis: a randomised, placebo controlled trial," Gut, 1997, 40: 485-491.
Burlina, Alberto B., "Long-Term Treatment with Sodium Phenylbutyrate in Ornithine Transcarbamylase-Deficient Patients," Molecular Genetics and Metabolism, 72, 351-355 (2001).
Butzner, J.D., "Butyrate enema therapy stimulates mucosal repair in experimental colitis in the rat," Gut, 1996, 38:568-573.
Chapman, M.A.S. et al., "Butyrate oxidation is impaired in the colonic mucosa of sufferers of quiescent ulcerative colitis," Gut, 1994, 35:73-76.
Heerdt, Barbara G. et al., "Potentiation by Specific Short-Chain Fatty Acids of Differentiation and Apoptosis in Human Colonic Carcinoma Cell Lines," Cancer Res., 1994,54:3288-3294.

Kemp, Stephan et al., "Gene redundancy and pharmacological gene therapy: Implications for X-linked adrenoleukodystrophy," Nature Medicine, vol. 4, No. 11, Nov. 1998, pp. 1261-1268.
Lupton, Joanne R., "Diet Induced Changes in the Colonic Environment and Colorectal Cancer," The Journal of Nutrition, 134, 479-482, 2004.
Mazzoni, Maurizio et al., "Supplemental Sodium Butyrate Stimulates Different Gastric Cells in Weaned Pigs 1-3", The Journal of Nutrition, 138, 1426-1431, 2008.
Musch, Mark W. et al., "IFN-γ down regulates expression of Na+/H+ exchangers NHE2 and NHE3 in rat intestine and human Caco-2/bbe cells," Am. J. Physiol. Cell Physiol., 280: C1224-C1232, 2001.
Nguyen, Toan D. et al., "Novel short chain fatty acids restore chloride secretion in cystic fibrosis," Biochemical and Biophysical Research Communications, 342 (2006) 245-252.
Olivieri, Nancy F. et al., "Treatment of thalassaemia major with phenylbutyrate and hydroxyurea," The Lancet, vol. 350, Aug. 16, 1997, pp. 491-492.
Rabbani, Golam H. et al., "Clinical Studies in Persistent Diarrhea: Dietary Management with Green Banana or Pectin in Bangladeshi Children," Gastroenterology, 2001, 121:554-560.
Rabbani, G.H. et al., "Short-Chain Fatty Acids Inhibit Fluid and Electrolyte Loss Induced by Cholera Toxin in Proximal Colon of Rabbit In Vivo," Digestive Diseases and Sciences, vol. 44, No. 8, Aug. 1999, pp. 1547-1553.
Ramakrishna, B.S. et al., "Amylase-Resistant Starch Plus Oral Rehydration Solution for Cholera," The New England Journal of Medicine, vol. 342, No. 5, Feb. 3, 2000, pp. 308-313.
Reich, Susanne et al., "Oral isobutyramide reduces transfusion in some patients with homozygous β-thalassemia," Blood, 2000, 96:3357-3363.
Reilly, K.J. et al., "Colonic short chain fatty acids mediate jejunal growth by increasing gastrin," Gut, 1995, 37:81-86.
Rubenstein, Ronald C. et al., "In Vitro Pharmacologic Restoration of CFTR-mediated Chloride Transport with Sodium 4-Phenylbutyrate in Cystic Fibrosis Epithelial Cells Containing ΔF508-CFTR", J. Clin. Invest., vol. 100, No. 10, Nov. 1997, 2457-2465.
Vernia, P. et al., "Combined Oral Sodium Butyrate and Mesalazine Treatment Compared to Oral Mesalazine Alone in Ulcerative Colitis," Digestive Diseases and Sciences, vol. 45, No. 5, May 2000, pp. 976-981.
Ginoux, Glaude, Written Opinion, European Patent Office, PCT/IT2009/000179, Oct. 26, 2010.
Baharlou, Simin, International Preliminary Report on Patentability, The International Bureau of WIPO, PCT/IT2009/000179, Oct. 26, 2010.

* cited by examiner

FATTY ACID DERIVATIVES FOR ORAL ADMINISTRATION ENDOWED WITH HIGH PALATABILITY

This application is a national phase patent utility filing under 35 USC §371, for international application no. PCT/IT2009/000179, filed on Apr. 21, 2009, which claims the benefit of priority to Italian patent application serial no. RM 2008 A 000214, filed Apr. 21, 2008. The aforementioned applications are explicitly incorporated herein by reference in their entirety and for all purposes.

FIELD OF THE INVENTION

The present invention relates to orally administrable fatty acid derivatives, in particular derivatives of butyric acid. The invention also relates to formulations containing them and clinical use thereof. More in particular, the invention relates to new compounds deriving from butyric acid, useful for all the known clinical applications of the latter and presenting with physicochemical characteristics suitable for easy oral administration, in that they are devoid of the unpleasant organoleptic properties that characterise butyrate. The new compounds, moreover, are easy to synthesize and are endowed with good solubility and storage stability

STATE OF THE ART

It is well known that short-chain fatty acids (SCFAs) are weak acids containing from 2 to 5 carbon atoms (pK 4.8), and that their endogenous production derives from the bacterial fermentation of oligo-polysaccharides and to a minimal extent of proteins, peptides and glycoproteins by the normal intestinal saprophytic flora. From the quantitative point of view, the main SCFAs deriving from the fermentation of carbohydrates are, in order and with reference to the corresponding anions, butyrate, acetate, propionate, formate, valerate and caproate, while isobutyrate, 2-methyl-isobutyrate and isovalerate are formed in lesser amounts through the catabolism of branched-chain amino acids (valine, leucine, isoleucine). From the quantitative point of view the SCFAs are the most important anions present in the colon lumen where they reach a total concentration of over 100 mM. Each SCFA has specific characteristics and distinctive physiological effects. Every day, at the intestinal level, one produce approximately 5 g of butyrate, which is present in the colon lumen at a concentration of 10-30 mM and is the main source of alternative energy to glucose, for the epithelial cells of the colon. Actually, 60-70% of the energy consumed by these cells derives from butyrate. It is also known that the dependence of the epithelial cells of the colon on butyrate as a source of energy increases going from the proximal to the distal colon. SCFAs are potentially absorbed by each intestinal digestive segment, as demonstrated in animal models and in human volunteers. Enterocytes are able to take up butyrate, propionate and acetate mainly through non-ionic diffusion and paracellular absorption. The absorption of these fatty acids has a significant impact upon the absorption of NaCl and in general upon the hydroelectrolytic balance. In particular, butyrate is able to exert a potent pro-absorptive stimulus at the intestinal level on the electroneutral transport of NaCl and a potent inhibitory effect on $Cl^-$ secretion. This pro-absorptive/antisecretory regulatory effect on the transepithelial transport of fluids occurs via a number of different mechanisms such as:

stimulation of NaCl absorption of through the combined action of two transport systems present on the brush border of the enterocyte, $Cl^-/HCO_3^-$ and $Na^+/H^+$ and $Cl^-$/butyrate and $Na^+/H^+$;

inhibition of $Cl^-$ secretion through inhibition of the activity of the co-transporter Na—K-2Cl (NKCC1) present on the basolateral side of the enterocyte.

In vitro studies have demonstrated that butyrate has an inhibitory effect on the secretion of $Cl^-$ induced by prostaglandin $E_2$, phosphocholine and cholera toxin. This effect is due to the reduced intracellular production of cyclic AMP secondary to the regulation of adenylate cyclase expression and activity. Comparative studies demonstrate that the pro-absorptive effect of butyrate in basal conditions and its inhibiting effect on potent secretory agents, are much greater in terms of both potency and duration of effect with respect to other SCFAs. In vivo studies in animals have demonstrated that butyrate has a preventive effect on possible inflammation at the intestinal level due to a diet rich in bran and fibres which may be able to be irritating for the intestinal mucosa. A confirmation of its efficacy is provided by the fact that, by favouring absorption, it enables pigs to achieve an optimal weight in shorter time periods (Mazzoni M et al., *J Nutr.* 2008 August; 138(8):1426-31; Biagi G et al., *J Anim Sci.* 2007 May; 85(5):1184-91. Epub 2007 Feb. 12). In man, butyrate is used as a dietary supplement in ulcerative rectocolitis due to its ability to reduce the number of diarrhoeal discharges and maintain good large bowel function.

In addition to the effects on the intestinal transepithelial transport of fluids, butyrate is a potent stimulant of trophism of the intestinal mucosa through vascular, hormonal and neuronal mechanisms. A reduction in butyrate concentrations at intestinal level is associated with increased mucosal inflammation and alterations of motility and of various functions involved in the mechanisms of growth, differentiation and mucosal repair, to the extent of giving rise to an increased risk of cancer. At the same time, butyrate is capable of negatively regulating the growth of intestinal tumour cells.

With specific reference to the field of gastroenterology, clinical studies carried out in children with acute diarrhoea induced by *V. cholerae* demonstrated a reduction in faecal volume and a faster recovery in patients who, in addition to receiving rehydrating therapy, introduced resistant amide precursors of SCFAs into their diet (Ramakrishna B S et al. *New. Engl. J. Med.* 2000; 324:308-313 16; Rabbani G H, et al., *Dig Dis Sci* 1999; 44:1547-1553). These results were also confirmed in other forms of infectious diarrhoea in children and in studies in animal models (Rabbani B S et al., *Gastroenterology* 2001; 121: 554-56; Alam N H et al., *Gastroenterology* 1997; 112:A; Alam N H et al., *Pediatr. Drugs* 2003; 5:151-165). The mechanisms of these therapeutic effects are attributable to the pro-absorptive action of the SCFAs, and particularly of butyrate, on the transepithelial transport of fluids at the intestinal level, able to counterbalance the faecal losses in the course of diarrhoea, thus reducing the duration and severity of the condition (Sellin J H et al., *Gastroenterology* 1998; 114:737-747; Mush M W et al. *Am. J. Physiol. Gastrointest. Liver Physiol.* 2001; 280:687-693). Due to its important regulatory effect on the absorption of fluids at the intestinal level, butyrate has been used successfully in patients with congenital chloridorrhoea, a severe autosomal recessive genetic disease characterised by severe chronic diarrhoea with neonatal onset (Berni Canani R et al., *Gastroenterology* 2004; 127:630-63423). This study shows that the oral administration of butyrate, at the dose of 100 mg/kg/day, is able to significantly reduce the number of evacuations/die and to increase the consistency of the stool, to a complete normalisation of bowel movements. This therapeutic effect comes both from stimulation of the Cl⁻/butyrate co-transporter and from regulation of the mechanisms of synthesis and expression, at the enterocyte plasma membrane level, of molecules responsible for the transepithelial transport of fluids in the intestine. These properties make the therapeutic use of butyrate plausible, also in other diseases of the gastrointestinal tract characterised by a defect in transport mechanisms of fluids and nutrients.

Butyrate also plays a central role in maintaining the integrity of the intestinal mucosa. In-vivo experiments in animal models demonstrated that butyrate has a trophic effect on the intestine, mediated by the increase in gastrin and dependent on the integrity of the sympathetic and parasympathetic nervous systems (Reilly K J et al. Gut 1995; 37:81-86). Its effects on the transepithelial transport of fluids and on the trophism of the intestinal mucosa make butyrate potentially the ideal therapeutic instrument for the prevention and cure of gastrointestinal disorders in the course of antibiotic therapy, and mainly for antibiotic-associated diarrhoea (AAD), which affects 15-40% of subjects taking this type of drugs (Mortensen P B et al., Scand. J. Gastroenterol. Suppl. 1996; 216:132-148; Krishnan S et al. Scand. J. Gastroenterol. 1998; 33:242-246). Again, the effects on transepithelial transport of fluids and on intestinal motility support the therapeutic use of butyrate in the treatment of gastrointestinal functional disorders characterised by altered motility, such as irritable bowel syndrome (Scarpellini E. et al., Dig. Liver Dis. 2007; Suppl.1: 19-22).

Evidence in the literature suggests a possible use of butyrate in the treatment of chronic inflammatory bowel diseases. Butyrate induces clinical and histological healing of experimental colitis induced in rat by means of trinitrobenzenesulphonic acid (Butzner J D et al., Gut 1996; 38:568-573). In the course of ulcerative rectocolitis (URC) there is an altered metabolism of SCFAs in the epithelial cells of the colon (Roediger W E W, Lancet 1980; 2:712-715), which causes low intra-luminal concentrations of these fatty acids. It has been postulated that the low SCFA concentrations found in patients with severe URC may contribute to the mucosal damage (Chapman M A S et al., Gut 1994; 35:73-76). In different clinical studies, butyrate administered locally (via enemas) in patients with URC gave positive results, accelerating the clinical, endoscopic and histological healing process, when administered in combination with other anti-inflammatory drugs such as mesalazine (Scheppach et al., Dig. Dis. Sci. 1991; 36:185-187; Bruer R I et al., Gut 1997; 40:485-491; Vernia P et al., Dig. Dis. Sci. 1995; 40:305-307). The efficacy of the butyrate/mesalazine combination was also confirmed in studies using orally administered formulations (Vernia P et al., Dig. Dis. Sci. 2000; 45: 976-981).

There is indication in the literature that populations with a low incidence of colon disease (also including colon cancer) have a diet rich in carbohydrates, the main precursors of SCFAs. The protective effect of butyrate against the development of colon cancer and polyposis is well documented both in in vitro and in-vivo studies: butyrate, in fact, is able to inhibit the growth of the main colon tumour cell lines in vitro, both by reducing proliferation and by stimulating differentiation and apoptosis. There is evidence of a direct antineoplastic effect of butyrate through regulation of the transcription of various genes involved in the process of oncogenesis (Boffa L et al., J. Biol. Chem. 1981; 256:9612-9621; Avivi-Green C et al., Oncol. Res. 2000; 12:83-95). However, this protective effect of butyrate is conditioned by the exposure time with respect to the tumorigenesis process (Basson M D et al., Proc. Soc. Exp. Biol. Med. 1998; 217: 476-483; Hague A et al., Int. J. Cancer 1993; 55:498-505; Heerdt B G et al., Cancer Res. 1994; 54:3288-3294; Lupton J R., Am. Soc. Nutr. Sci. 2004; 134:479-482).

Sodium-4-phenylbutyrate (4PBA), an analogue of butyrate administered orally, is regarded as a potential drug for the treatment of cystic fibrosis (in patients with a AF 508 mutation. Actually, 4PBA, and, more recently, 2,2-dimethylbutyrate (ST20) and alpha-methyl-hydro-cinnamic acid (ST7), are able to induce increased expression of CFTR at the respiratory epithelial level both in vitro and in vivo (Rubenstein R C et al., J. Clin. Invest. 1997; 100:2457-2465; Nguyen T D et al., Biochem. Bioph. Res. Com. 2006; 342:245-252).

In the field of haematology, butyrate is known to be an inducer of the production of foetal haemoglobin (HbF) through selective stimulation of the activity of genes coding for gammaglobin chains (Ikuta T et al., Blood 1998; 92:2924-2933). This action led to its use in patients with intermediate β-thalassaemia, in whom a slight increase in HbF induces a reduction of extramedullary haemopoiesis with a significant reduction of morbidity and improvement in the quality of life (Olivieri N F et al., Lancet 1997; 350:491-492; Faller D V et al., Curr. Opin. Hematol. 1995; 2:109-117).

In the first trials carried out in thalassaemic patients, compliance with treatment was poor because intravenous infusions were needed for 4 days at intervals of 3-4 weeks. It was later demonstrated that orally active butyric acid compounds (sodium phenylacetate and sodium-4-phenylbutyrate) were able to increase the production of HbF in subjects with sickle-cell anaemia. Oral treatment with isobutyramide, at the dose of 350 mg/kg/die in patients suffering from β-thalassaemia prolonged the transfusion interval and reduced the iron overload. Currently, however, the use of butyrate and its analogues beside controlled clinical trials is not widespread owing to the poor compliance demonstrated also with the oral formulations.

With reference to genetic metabolic diseases, sodium-4-phenylbutyrate has been approved by the US Food and Drug Administration (FDA) for use in patients with a deficit of enzymes of the urea cycle, in which it acts as an ammonia scavenger. In fact, sodium 4-phenylbutyrate is oxidised to phenylacetate, which binds to glutamine and causes its urinary excretion. In patients with ornithine transcarbamylase deficiencies, the use of sodium-4-phenybutyrate affords better metabolic control and a greater intake of natural proteins with the diet (Burlina A B et al., Molecular Genetics and Metabolism 2001; 72:351-355). Also under investigation is the possible use of sodium-4-phenylbutyrate in the treatment of X-linked adrenoleukodystrophy (X-ALD), a peroxisoma disorder characterised by altered metabolism and accumulation of very long chain fatty acids. Sodium-4-phenylbutyrate, whether used in vitro on fibroblasts of patients with X-ALD, or in vivo on X-ALD knockout guinea-pigs, brings about an increase in the beta-oxidation of very long chain fatty acids and induces the proliferation of peroxisomes (Kemp S et al., Nat. Med. 1998; 4:1261-1268).

Finally, it has been demonstrated more recently that the oral administration of butyrate is able to prevent and treat insulin resistance and weight increase in an obese rat animal model. These effects are at least partly attributable to the stimulation of energy expenditure and of a number of mitochondrial functions and open up interesting new prospects of use in the field of the prevention and treatment of metabolic disorders associated with obesity.

From the scientific data in the literature and from the clinical experience of a number of research teams, a broad spectrum of possibilities emerges for the therapeutic use of butyrate by oral administration and a lack of important adverse events.

Some butyrate-based products are available on the market, but their use is still very much limited and greatly undersized in relation with the broad spectrum of possible indications, especially in chronic diseases where a long-term use of the compound is forseen. The main problem is due to difficulties regarding the availability of butyrate formulations which are easy to administer orally, especially for paediatric subjects and, above all, to the extremely poor palatability of the products currently available on the market. The extremely unpleasant taste and odour make the oral administration of the butyrate-based products currently available extremely difficult, and these difficulties are even more marked in paediatric subjects, where the administration of such products proves very difficult indeed. The Problems relating to possible pharmaceutical formulations of butyrate stem from the fact that the product presents particular physicochemical characteristics. Butyric or n-butanoic acid ($C_4H_8O_2$), at room temperature, presents as a dense liquid characterised by a very unpleasant, intense odour of stale cheese, and with time undergoes degradation phenomena that alter its stability. In this form the oxidative phenomena are more evident, and the normal pharmaceutical forms (syrups, capsules and tablets) are inapplicable, with the exception, within certain limits, of soft gelatine capsules, whose use, however, is not possible in sucklings and in early infancy. The most easily obtainable derivatives of butyric acid are the salts of alkaline and alkaline-terrous metals, which, in turn, present by no means negligible drawbacks. Sodium salts present themselves as solids with a fair degree of hygroscopicity and a strong butyric odour. Calcium salts, despite having a solid form, have very poor solubility in water and the magnesium salts, also solids, are deliquescent. Calcium and magnesium salts, anyway, also keep their strong characteristic odour. The literature cited above provides abundant evidence of the drawbacks relating to the extremely unpleasant taste and odour and the related epigastric disorders due to the oral intake of butyrate or its derivatives, and of its straight- or branched-chain analogues with up to 6 carbon atoms. This happens, for example, with the administration of sodium phenylbutyrate or isobutyramide in clinical studies of thalassaemic patients (Collins A F et al., *Blood* 1998; 85:43-49; Reich S et al., *Blood* 2000; 96:3357-3362). Based on the foregoing considerations, there is an obvious need to have available butyrate formulation (or a formulation of straight- or branched-chain fatty acids with up to 6 carbon atoms) that keeps its therapeutic efficacy, but that at the same time allows an easy oral administration of the product, also thanks to a better palatability, while presenting limited costs. Such a product would lend itself optimally to long-term treatments and would also be useful in the medical field. Considering the possible chemical modifications of butyric acid to obtain a derivative that presents characteristics of good stability and solubility, lack of odour and taste and acceptable palatability, and that is non-hygroscopic in the solid state and is easy to synthesize and purify, it may be noted that the chlorides of fatty acids react rapidly in an anhydrous milieu both with alcohol and amine groups, yielding as reaction products, esters and a number of pharmacologically active molecules. Esters present the advantage of having a pleasant odour, to the extent that the methyl and ethyl esters of butyrate are used as flavouring and aromatising agents in the food field, but they present generally as oils or low-melting deliquescent solids, and this does not solve the difficulties due to the liquid state, nor those of their stability in air. Moreover, the esterified form is poorly stable in an acid milieu, and at the gastric pH, hydrolysis brings about formation of the acid and alcohol from which these esters derive, with consequent release of butyric acid, again-presenting, albeit to a lesser extent, with the above-mentioned problems of palatability. Ester derivatives of butyrate are described, for example, in U.S. Pat. No. 5,763,488, which, for clinical use in β-haemoglobin diseases, proposes the oral administration of prodrugs consisting of butyrate esters with threitol. Such derivatives are proposed with the aim of improving the bioavailability of butyrate, but the document does not take into consideration the aspects relating to the palatability of oral drugs based on this active ingredient.

With specific reference to gastrointestinal diseases, the international patent application No. WO 98/40064 proposes the use, by oral administration, of butyrate prodrugs with lactic acid. The aim is to overcome the disadvantages due to the poor pharmacokinetic properties of butyrate and to obtain oral drugs that offer a good bioavailability and a satisfactory half-life, allowing effective release of butyrate into the plasma. Also in this case, the document does not take into consideration the aspect of the palatability of a butyrate-based oral drug. It has now been found that some amide derivatives of SCFAs, and particularly of butyric acid, solve the above-mentioned problems.

BRIEF DESCRIPTION OF THE FIGURES

FIG. 1 shows the effects of Na butyrate addition on Isc in Caco-2 cells mounted in an Ussing chamber. The decrease in Isc caused by the addition of Na butyrate on the mucosal side indicates ion absorption. Data are expressed as means of three experiments. The substance was added at time zero;

FIG. 2 shows the effects of compound 1 addition (example 1) on Isc in Caco-2 cells mounted in an Ussing chamber. The decrease in Isc caused by the addition of compound 1 on the mucosal side indicates ion absorption. Data are expressed as means± of three experiments. The substance was added at time zero;

FIG. 3 shows the effects of compound 2 addition (example 1) on Isc in Caco-2 cells mounted in an Ussing chamber. The decrease in Isc caused by the addition of compound 2 on the mucosal side indicates ion absorption. Data are expressed as means± of three experiments. The substance was added at time zero;

FIG. 4 shows the effects of compound 3 addition (example 1) on Isc in Caco-2 cells mounted in an Ussing chamber. The decrease in Isc caused by the addition of compound 3 on the mucosal side indicates ion absorption. Data are expressed as means± of three experiments. The substance was added at time zero;

FIG. 5 shows the effects of the addition of the mixture of compounds 1, 2 and 3 (example 1) on Isc in Caco-2 cells mounted in an Ussing chamber. The decrease in Isc caused by the addition of the mixture of compounds 1, 2 and 3 on the mucosal side indicates ion absorption. Data are expressed as means± of three experiments. The substance was added at time zero.

DETAILED DESCRIPTION OF THE INVENTION

Figure 1:
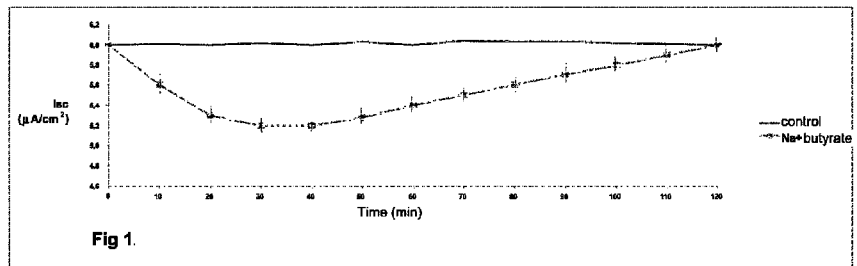
FIGS. 1-5 show the variations in short circuit current (Isc) as a function of time (min.). The effect was dose-dependent. In particular.

In the context of the studies that have led to the present invention, it was considered that the amide derivatives of SCFAs, particularly of butyric acid, generally present themselves in a solid, odourless and tasteless form, are more stable than the esters at gastric pH, and are able to release the corresponding acid by alkaline hydrolysis at the level of the small and large bowel. This pharmacokinetic characteristic renders these derivatives potential prodrugs with particular properties in terms of prolonged release in the intestine, which constitutes a very important therapeutic target, responding in a particularly effective manner to the need for accurate drug targeting.

According to the invention, it has been found that the synthesis of straight- and branched chain SCFA amides, using highly biocompatible molecules devoid of toxicity, such as naturally occurring amino acids, and among the latter particularly phenylalanine, provides derivatives endowed with all the organoleptic and physicochemical characteristics required for optimal use of the final product as an oral drug indicated in the medical field, also for long-term therapy or for the treatment of chronic diseases. Among the various most abundantly available naturally occurring amino acids, phenylalanine provides the best amide derivative for its organoleptic and physicochemical characteristics, yielding odourless and colourless solid crystalline products and allows particularly economic purification in terms of cost:yield ratio. Particularly preferred, according to the invention, is an acid-stable butyrate amide with the amino acid phenylalanine, phenylalanine-butyramide (FBA), which presents itself as a solid, poorly hygroscopic, form easy to weight, stable to acids and alkalis and able to release butyric acid at the small and large bowel level in a constant manner over time. This product, for which the toxicity studies referred to here below have demonstrated a toxicological profile comparable to that of butyrate, presents with physicochemical features distinctly more suitable for extensive clinical use than the latter. A particular aspect of FBA is that it does not have the unpleasant odour of butyrate and is practically tasteless, thus allowing to overcome the main limitation to the use of butyrate in the therapeutic field, namely its very poor palatability. Moreover, the solubility of FBA in water is satisfactory since it produces clear solutions up to the concentration of 0.1 M and suspensions at higher concentrations.

The amide derivative of butyric acid with phenylalanine, or suitable derivatives of the latter, is prepared by reacting the appropriate phenylalanine derivative with butyroyl chloride, or an equivalent derivative of butyric acid (simple or mixed ester or anhydride)—see Y in claim 1) in an aprotic polar inert organic solvent, at room temperature. Following this reaction the monobutyroyl derivative is formed, which is the main component in quantitative terms, accompanied, according to the structure of the starting products, also by the dibutyroyl derivative of the initial phenylalanine compound and other derivatives, resulting, for example, from the cyclisation of the main product during the reaction.

Although it is possible to isolate and purify the compounds obtains by means of known techniques, it has also been observed, according to the invention, that the reaction mixture can be advantageously applied without prior separation into the individual constituent components and that also in this state it shows the desired physicochemical, organoleptic and pharmacokinetic properties.

It is therefore a specific object of the present invention to provide an amide derivative of an SCFA obtainable by the reaction of a derivative of said fatty acid with a phenylalanine derivative according to the following general formula:

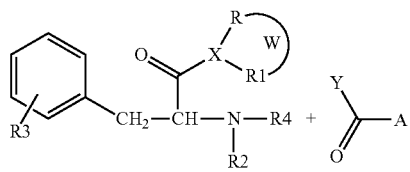

wherein:

Y represents an atom of halogen, alkoxyl (2-6 carbon atoms), acyl (2-6 carbon atoms);

A represents a straight or branched $C_{(1-5)}$ alkyl chain, possibly substituted with phenyl;

X represents oxygen, nitrogen or sulphur, with the proviso that:
when X represents oxygen or sulphur, R represents hydrogen or a $(C_{1-6})$ alkyl group, and $R_1$ and W are nil;
when X represents nitrogen,
R and $R_1$ independently represent, hydrogen or a $(C_{1-6})$ alkyl group or a $(C_{1-6})$ acyl group and W is nil; or
W represents a 1,2-alkylene chain with 2 to 6 carbon atoms and R and $R_1$ are methylene groups;

$R_2$ and $R_4$ independently represent, hydrogen or a $(C_{1-6})$ alkyl group or a $(C_{1-6})$ acyl group;

$R_3$ is selected from the group consisting of H, $(C_{1-6})$alkyl, $(C_{1-6})$alkoxyl, halogen, oxidryl, cyano, nitro, amino, mono- or di-$(C_{1-6})$alkylamino, $(C_{2-6})$acylamino, formyl, hydroxyiminomethyl, $(C_{1-6})$alkoxyiminomethyl and carbamoyl;

with the following provisos: taking as understood what has been described above, the derivatives according to the present invention include their salts with pharmaceutically acceptable bases or acids and their possible diastereoisomeric and enantiomeric forms.

The $C_1$-$C_6$ alkyl groups defined for the purposes of the present invention can be straight or branched, and are essentially methyl, ethyl, propyl, isopropyl, butyl, isopentyl, n-hexyl and analogues thereof, whereas the $C_1$-$C_6$ alkoxyl groups are preferably selected from the group consisting of methoxyl, ethoxyl, propoxyl, isopropoxyl, butoxyl, 2-methylpropoxyl and tert-butoxyl.

Again for the purposes of the present invention, an alkylene chain can be straight or branched, such as, for example, ethylene, 1,3-propylene, 2-methylethylene, 1,4-butylene, 2-methyl-1,3-propylene, 2-ethyl-ethylene, 1,5-pentylene, 2-ethyl-1,3-propylene, 2-methyl-1,4-butylene and the like, whereas by halogen it is essentially meant fluorine, chlorine, bromine and iodine. In the manner of, and in conformity with the current chemical nomenclature, a $C_2$-$C_6$ acyl group essentially identifies acetyl, propionyl, butyroyl, pentanoyl, pivaloyl, hexanoyl and the like. The terms alkoxyl, alkylamino, acylamino, alkoxyiminomethyl and carbamoyl also have meanings in conformity with the nomenclature in the art.

The compounds according to the invention are prepared by reacting the two compounds indicated above, preferably in substantially equimolecular amounts, in an aprotic polar inert organic solvent such as, for example, benzene, toluene or chloroform at room temperature of the reaction mixture, preferably for a time period from four to twenty-four hours, followed by one or more separation and purification stages of the product obtained, preferably by recrystallisation. In case the phenylalanine derivative are reacted and the butyroyl derivative, a mixture of butyryl derivatives will be obtained, where the main product will consist in the monoderivative with other reaction products such as the dibutyryl derivative and the cyclic derivative indicated here in below.

According to some specific embodiments, it is an object of the invention an amide derivative of a short chain fatty acid having the following general formula:

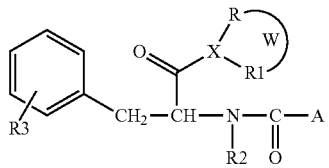

(I)

wherein A, X, W, R, $R_1$, $R_2$ and $R_3$ have the same meanings indicated above, and the corresponding salts with pharmaceutically acceptable bases, as well as the possible diastereoisomeric and enantiomeric forms.

A few preferred forms of the compound of formula (I) illustrated also in the following synthesis examples are the formula (I) compound wherein A represents —$(CH_2)_2CH_3$, X represents nitrogen and R, $R_1$, $R_2$ and $R_3$ represent hydrogen (N-(1-carbamoyl-2-phenyl-ethyl)butyramide) and the one where A represents —$(CH_2)_2CH_3$, X represents oxygen, R represents a methoxyl group, and $R_2$ and $R_3$ represent hydrogen (methyl ester of 2-butyrylamino-3-phenylpropionic acid).

According to another specific embodiment, it is the object of the present invention a mixture of amide derivatives of butyric acid obtainable by reaction of a butyroyl halide with a phenylalanine derivative according to the scheme defined above, and their salts with pharmaceutically acceptable bases or acids, as well as their possible diastereoisomers and enantiomers. Particularly advantageous for the purposes of the invention is a mixture obtained by carrying out the process described in example 1 and substantially comprises the following three compounds:

N-(1-carbamoyl-2-phenyl-ethyl)butyramide (compound 1), of formula:

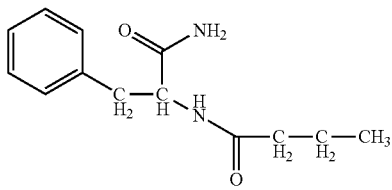 [SMILES: CCCC(=O)NC(Cc1ccccc1)C(N)=O]

N-(1-butyroyl-carbamoyl-2-phenyl-ethyl)butyramide (compound 2), of formula:

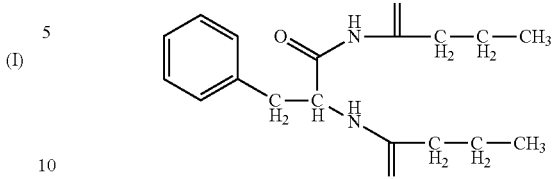

5-benzyl-2-propyl-1H-imidazol-4(5H)-one (compound 3), of formula:

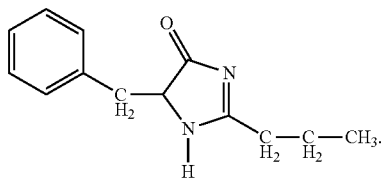 [SMILES: CCCC1=NC(=O)C(Cc2ccccc2)N1]

The compounds thus obtained can be used in mixtures thereof or can be isolated and purified according to known techniques. They can be isolated both as free forms and as the corresponding salts of pharmaceutically acceptable bases or acids, adding a suitable amount of the chosen base or acid to the free forms or to the reaction milieu. Examples of such salts are pharmaceutically acceptable sodium and potassium salts, ammonia salts, ethylenediamine and aliphatic or aromatic nitrogen bases, hydrochlorides, sulphates, aliphatic or aromatic acids. The compounds of the invention, bearing in mind the nature of the substituents A, X, R, $R_1$, $R_2$ and $R_3$, as well as the phenyl group, show at least one chiral centre; therefore, they may exist as racemic forms or as possible diastereoisomers forms that can be obtained with procedures familiar to the expert chemist. For example, one of these involves preparatory chromatography on plates with a chiral support, using an appropriate eluent system. As said before, the possible diastereoisomers of the compounds of formula (I) constitute a further subject matter of the present invention. It is important to note that the compounds identified, as well as their salts with pharmaceutically acceptable bases or acids, keep the effects at intestinal level that were previously described in relation to butyrate. The experimental data for this check were obtained in in-vitro models of human intestinal epithelium. In another aspect, it is object of the invention the use of one or more amide derivatives of short-chain fatty acids, particularly derivatives of butyric acid obtainable by the reaction described above, or of mixtures thereof, for the manufacture of a pharmaceutical preparation, and more particularly a preparation useful for the treatment and prevention of human or animal diseases.

The possible therapeutic uses of the compounds according to the invention are summarised in the following table.

TABLE

| Therapeutic indications for short chain fatty acids | |
|---|---|
| Gastroenterological diseases | Gastrointestinal tumours; acute gastroenteritis; chronic non-specific diarrhoea; traveller's diarrhoea; antibiotic-associated diarrhoea; irritable bowel syndrome; cholera; congenital chloridorrhoea; congenital sodium diarrhea; chronic secretory diarhea; cystic fibrosis; chronic inflammatory bowel disease (CIBD); malnutrition-induced enteropathy; mucosal atrophy induced by total parenteral nutrition; enteropathy induced by radiotherapy or chemotherapy; short bowel syndrome and intestinal insufficiency; prevention and treatment of colon adenocarcinoma; intestinal polyposis; pouchitis; allergic enterocolitis |

TABLE-continued

Therapeutic indications for short chain fatty acids

| | |
|---|---|
| Haematological disases | intermediate β-thalassaemia; sickle-cell anemia |
| Genetic metabolic diseases | ornithine transcarbamylase deficiency; X-linked adrenoleukodystrophy (X-ALD), |
| Obesity | insulin resistance; metabolic sindrome |

Finally, the pharmaceutical compositions of the invention comprise as the active ingredient at least one compound of the general formula (I) and correspond derivatives thereof, preferably at least one of the amide derivatives of butyric acid defined above, or more preferably the mixture of the three compounds 1, 2 and 3, together with one or more pharmacologically acceptable adjuvants and/or vehicles. As said in the introduction, the type of composition of the invention that proves most advantageous for the therapeutic purposes indicated is a composition formulated for oral administration, which makes it possible to improve patient compliance, especially in chronic therapies and in paediatric or veterinary use. Pharmaceutical preparations suitable for oral administration may, for example, be in the form of tablets, capsules, syrups, solutions and drinkable suspensions, drops, granulates, preparations for sublingual administration or in topical, cutaneous or gastrointestinal formulations, or preparations administrable parenterally, also in combination with other active ingredients including drugs, dietary supplements, functional foods, nutraceuticals and medical devices.

The specific features of the invention, as well as the advantages of the same and the corresponding mode of chemical synthesis, will be more evident with reference to the detailed description presented merely as a series of examples here below, together with the results of the experiments carried out on it and the data comparing it with the prior art.

EXAMPLE 1

Synthesis Method 0.01 mol of phenylalanine carboxamide and 0.01 mol of butyroyl chloride were dissolved in 50 ml of chloroform and the resulting mixture was left to react at room temperature for twenty-four hours.

The mixture, evaporated in vacuo, yielded a solid white-coloured residue which was washed with a 1% sodium bicarbonate solution. The aqueous bicarbonate solution was extracted twice with an equal volume of ethyl acetate to recover an additional fraction of the derivatives mixture. To isolate the single components, the mixture thus treated was processed chromatographically on a silica gel column, using dichloromethane as the eluent, obtaining the three compounds characterised here below. All three compounds were recrystallised With a mixture of chloroform/n-hexane 1:1 v:v, obtaining a final yield equal to or greater than 50% of compound 1, and similar percentages of compounds 2 and 3.

Compound 1:
N-(1-carbamoyl-2-phenyl-ethyl)butyramide

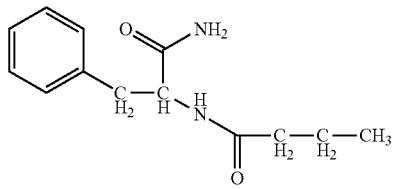 [SMILES: CCCC(=O)NC(Cc1ccccc1)C(N)=O]

$^1$H-NMR: 7.34-7.22 (5H, m); 6.23 (1H, bd); 5.99 (1H, NH$_2$); 5.54 (1H, NH$_2$); 4.71 (1H, dd); 3.06 (2H, dd); 2.11 (2H, t); 1.59 (2H, t); 0.87 (3H, q).

M.p.: 186-9° C. C.M.W. 234. (Calculated Molecular Weight)

Yield: ≥50% by weight on the total of the three compounds.

Compound 2:
N-(1-butyroyl-carbamoyl-2-phenyl-ethyl)butyramide

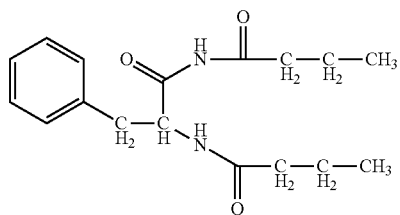 [SMILES: CCCC(=O)NC(=O)C(Cc1ccccc1)NC(=O)CCC]

$^1$H-NMR: 9.25 (1H, bs); 7.25-7.18 (5H, m); 6.38 (1H, bd); 4.97 (1H, m); 2.18 (1H, dd); 2.89 (1H, dd); 2.58 (2H, t); 2.15 (2H, t); 1.59 (4H, m); 0.92 (3H, t). 0.82 (3H, 7).

M.p.: 198-9° C. C.M.W. 304

Yield: ≃20-30% by weight on the total of the three compounds.

Compound 3:
5-benzyl-2-propyl-1H-imidazol-4(5H)-one

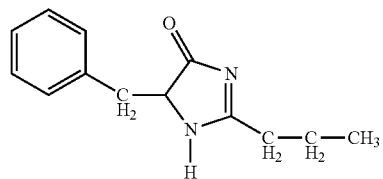 [SMILES: CCCC1=NC(=O)C(Cc2ccccc2)N1]

$^1$H-NMR: 7.34-7.22 (5H, m); 5.88 (1H, bd); 5.20 (1H, m); 3.08 (2H, dd); 2.18 (2H, t); 2.11 (2H, t); 1.61 (2H, m); 0.87 (3H, t).

M.p.: 151-2° C. C.M.W. 216

Yield: ≃20-30% by weight on the total of the three compounds.

EXAMPLE 2

Compound 4:
N-(1-carbamoyl-p-toluyl-methyl)butyramide

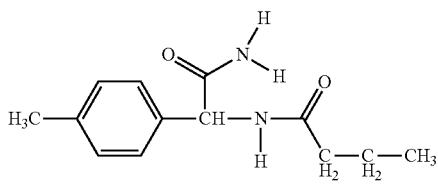 [SMILES: CCCC(=O)NC(C(N)=O)c1ccc(C)cc1]

0.01 mol of 2-amino-2-p-toluylacetamide and 0.015 mol of butyroyl chloride were dissolved in 50 ml of chloroform with the addition of 0.02 mol of triethylamine and the resulting mixture was left to react at room temperature for twenty-four hours. The mixture, evaporated in vacuo, yielded a solid white-coloured residue which was washed with a 1% sodium bicarbonate solution. The aqueous bicarbonate solution was extracted twice with an equal volume of ethyl acetate to recover an additional fraction of compound 4. Compound 4 was recrystallised with a mixture of chloroform/n-hexane 1:1 v:v, obtaining a final yield of 90%.

EXAMPLES 3 AND 4

Compound 5:
N-(2-carbamoyl-1-phenyl-ethyl)butyramide

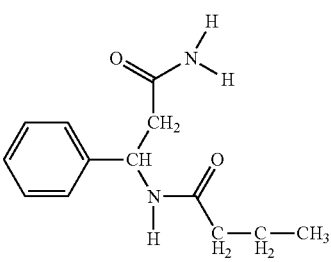 [SMILES: CCCC(=O)NC(CC(N)=O)c1ccccc1]

Compound 6:
N-(4(2-carbamoyl-ethyl)phenyl)butyramide

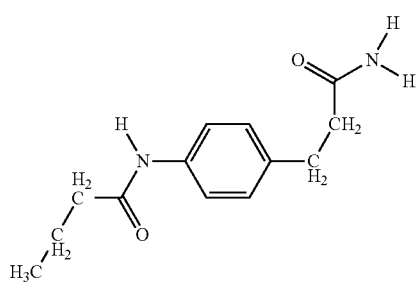 [SMILES: CCCC(=O)Nc1ccc(CCC(N)=O)cc1]

Compounds 5 and 6 were prepared in the same way as compound 4 in example 2 using 0.01 mol of 3-amino-3-phenyl-propanamide and 3-(4-aminophenyl)propanamide, respectively, and obtaining a final yield of 90%.

EXAMPLE 5

Compound 7: N-(1-oxo-3-phenyl-1-(piperidin-1-yl)propan-2-yl)butyramide

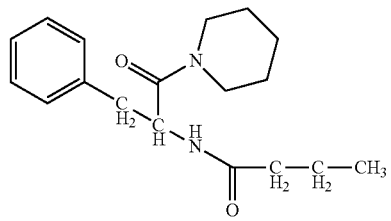 [SMILES: CCCC(=O)NC(Cc1ccccc1)C(=O)N1CCCCC1]

Compound 7 was prepared in the same way as compound 4 in example 2, using 0.01 mol of 2-amino-3-phenyl-1-(piperidin-1-yl)propan-1-one and recrystallising with a mixture of chloroform/n-hexane 2:1 v:v. A final yield of 90% is obtained

EXAMPLES 6-14

Compound 8: N-(1-oxo-3-phenyl-1-(pirrolidin-1-yl)propan-2-yl)butyramide

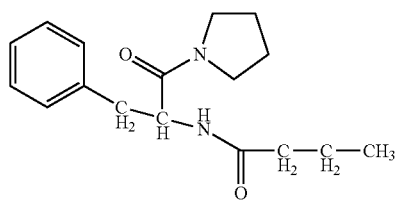 [SMILES: CCCC(=O)NC(Cc1ccccc1)C(=O)N1CCCC1]

Compound 9: N-(1-(methylcarbamoyl)-2-phenylethyl)butyramide

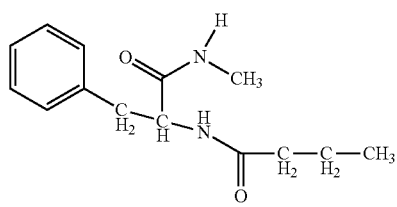 [SMILES: CCCC(=O)NC(Cc1ccccc1)C(=O)NC]

Compound 10:
N-(1-(ethylcarbamoyl)-2-phenylethyl)butyramide

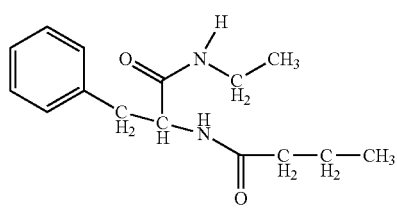 [SMILES: CCCC(=O)NC(Cc1ccccc1)C(=O)NCC]

Compound 11:
N-(1-(propylcarbamoyl)-2-phenylethyl)butyramide

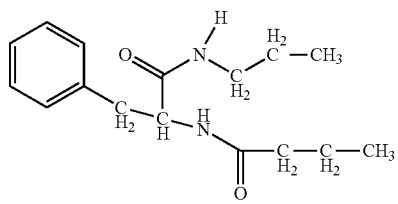 [SMILES: CCCNC(=O)C(Cc1ccccc1)NC(=O)CCC]

Compound 12:
N-(1-(butylcarbamoyl)-2-phenylethyl)butyramide

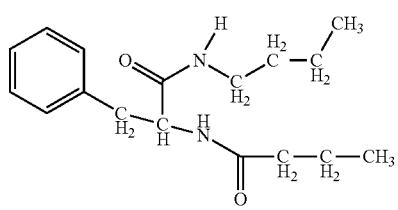 [SMILES: CCCCNC(=O)C(Cc1ccccc1)NC(=O)CCC]

Compound 13:
N-(1-(pentylcarbamoyl)-2-phenylethyl)butyramide

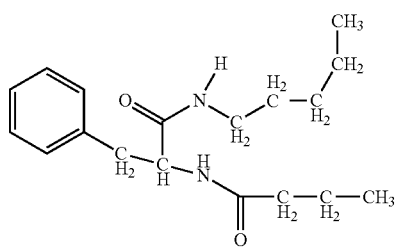 [SMILES: CCCCCNC(=O)C(Cc1ccccc1)NC(=O)CCC]

Compound 14:
N-(1-carbamoyl-2-phenylethyl)-N-methyl-butyramide

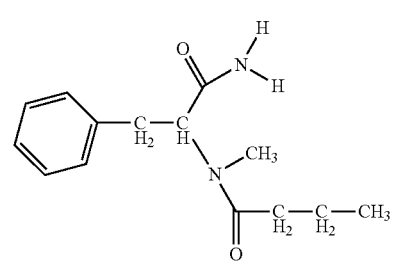 [SMILES: CCCC(=O)N(C)C(Cc1ccccc1)C(N)=O]

Compound 15:
N-(1-carbamoyl-2-phenylethyl)-N-ethylbutyramide

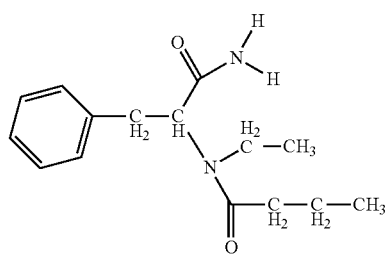 [SMILES: CCCC(=O)N(CC)C(Cc1ccccc1)C(N)=O]

Compound 16:
N-(1-carbamoyl-2-phenylethyl)-N-propylbutyramide

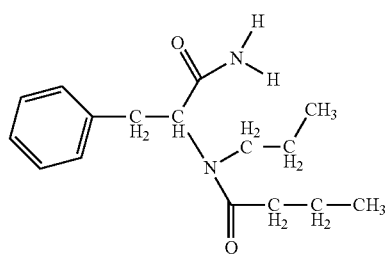 [SMILES: CCCC(=O)N(CCC)C(Cc1ccccc1)C(N)=O]

The compounds 8-16 were prepared in the same way as compound 7 in example 5 using 0.01 mol of:

2-amino-3-phenyl-1-(pyrrolidin-1-yl)propan-1-one for compound 8;

2-amino-N-methyl-3-phenyl-propanamide for compound 9;

2-amino-N-ethyl-3-phenyl-propanamide for compound 10;

2-amino-3-phenyl-N-propyl-propanamide for compound 11;

2-amino-N-butyl-3-phenyl-propanamide for compound 12;

2-amino-N-pentyl-3-phenyl-propanamide for compound 13;

2-(methylamino)-3-phenyl-propanamide for compound 14;

2-(ethylamino)-3-phenyl-propanamide for compound 15;

3-phenyl-2-(propylamino)propanamide for compound 16;

and obtaining a final yield of 90% for each compound prepared.

Similarly, as in the preparation of the products described in examples 1-14, amides were prepared, substituting isobutyroyl, valeroyl, isovaleroyl, phenylbutyroyl and phenylvaleroyl chloride for the butyroyl chloride.

EXAMPLE 15

Methyl ester of 2-butyrylamino-3-phenylpropionic acid

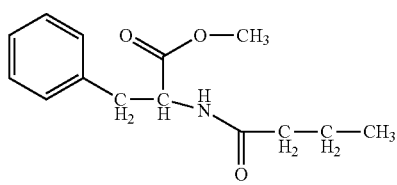 [SMILES: CCCC(=O)NC(Cc1ccccc1)C(=O)OC]

0.01 mol of phenylalanine methyl ester and 0.01 mol of butyroyl chloride were dissolved in 50 ml of anhydrous dichloromethane and the resulting mixture was left to react at room temperature for four hours.

The mixture, evaporated in vacuo, yielded an oily residue which was washed with a 1% sodium bicarbonate solution. The compound thus obtained was purified by chromatography using chloroform as the eluent. Yield: 85% of titered product. Oil.

$^1$H-NMR: 7.25 (3H, t+t); 7.07 (2H, d); 6.09 (1H, bd); 4.82 (1H, dd); 3.69 (3H, s); 3.08 (2H, dd); 2.12 (2H, t); 1.59 (2H, t); 0.87 (3H, q).

Toxicity Study of the Compounds in Example 1

The compounds of the reaction mixture obtained according to example 1 were submitted to toxicological study either alone or in combination, after separation from the mixture and purification. The toxicity data obtained were compared with those of non-derivatised butyric acid.

The LD50 of butyric acid, measured in Swiss mice of both sexes weighing 30 g was 8.8 g/kg after oral administration.

The reaction mixture of Example 1 showed the following percentage composition:

Compound 1: 50%
Compound 2: 25%
Compound 3: 25%.

The LD50 of the mixture was 19.93 g/kg after oral administration equivalent to 8.8 g of butyric acid.

The compounds tested as single compounds yielded the following results:

Compound 1 LD50 23.78 g/kg equivalent to 8.8 g of butyric acid

Compound 2 LD50 16.29 g/kg equivalent to 8.8 g of butyric acid

Compound 3 LD50 21.62 g/kg equivalent to 8.8 g of butyric acid.

In conclusion, both the mixture and the single compounds show an LD50 equivalent to that of butyric acid as reported in the Merck Index, 12th edition.

Effects of Sodium Butyrate and of Compounds 1, 2 and 3 on the Trans-Epithelial Transport of Water and Electrolytes Cell Cultures The experiments were carried out using a human intestinal cell line called Caco-2, obtained from the American Type Culture Collection (ATCC, Rockville, USA). These cells, 15 days after confluence, form a monolayer of enterocytes with morphological and functional features identical to those of ileal enterocytes at the apex of the villus (Berni Canani R, et al. *Gastroenterology* 2003; 124:368-76). Cells were grown in a culture medium consisting in Dulbecco's Modified Eagle's Medium (DMEM) containing glucose (4.5 g/L), 10% Fetal Calf Serum (FCS), 1% non-essential amino acids, 1% L-glutamine, 1% sodium pyruvate, streptomycin (50 mg/ml), penicillin (50 mU/ml), and were incubated at 37° C. in an atmosphere of 5% $CO_2$ and 95% $O_2$. The culture medium was replaced every day.

Experiments with the Ussing Chamber

For all the experiments were used cells at the 30th-40th pass, $2\times10^6$ cells per filter, grown on polycarbonate supports (pore size 0.4 µm, diameter 24.5 mm) for 15 days post-confluence. Each support containing the cells was mounted in an Ussing chamber (World Precision Instruments, Sarasota, Fla.) as a cellular monolayer between the luminal and the serosal compartments (Berni Canani R, et al. *J. Pediatr. Gastroenterol. Nutr.* 28: 315-320, 1999). The Ussing chamber system, allows through the measurement of defined electrical parameters, the study of transepithelial transport of water and electrolytes. These parameters consist in: 1) transepithelial potential difference (PD) and short circuit current (Isc), an expression of the transepithelial passage of ions; 2) resistance (RT) and, ionic conductance (G), a measure of tissue integrity. An absorptive-type stimulus on transepithelial transport induces a decrease in Isc, whereas a secretory-type stimulus induces an increase in Isc. The Isc is expressed in microamperes per square centimeter ($\mu A/cm^2$), conductance in millisiemens per square centimeter ($mS/cm^2$) and the transepithelial potential difference in millivolts (mV). Measurement of these electrical parameters is made possible by the presence of silver electrodes, placed proximally to both sides (serosal and luminal) of the cellular monolayer and connected with an automatic voltage system equipped with software for data acquisition and processing (DVC 1000, World Precision Instruments, Sarasota, Fla., USA). Each compartment contained 10 ml of Ringer's solution with the following composition (in mmol/L): NaCl, 114; KCl, 5; $NaH_2PO_4$, 0.3; $Na_2HPO_4$, 1.65; $CaCl_2$, 1.25; $MgCl_2$, 1.1; $NaHCO_3$, 25; glucose, 10. The incubation liquid was circulated through the chamber by means of the flow of a gaseous mixture composed of 95% $O_2$ and 5% $CO_2$ and was maintained at a temperature of 37° C. by means of a thermostat (Berni Canani R. et al. *J. Pediatr. Gastroenterol. Nutr.* 28: 315-320, 1999). The study of changes in electrical parameters reflecting changes in transepithelial transport of water and electrolytes was carried out in baseline conditions and after administration of the compounds on the luminal side of the monolayer of Caco-2 cells.

Then, to study the effects of the compounds on the transepithelial transport of water and electrolytes in conditions of active secretion induced by a secretagogue agent, experiments were carried out where the enterocytes were co-incubated simultaneously with the compounds and with cholera toxin (CT) as an agonist of the main route of transduction of the signal responsible for the secretion of fluids at the intestinal level (Berni Canani R, et al. *J. Infect. Dis.*, 2005; 191: 1072-1077). Finally, cell viability was evaluated by measuring the electrical response to the addition of theophylline (5 mM) on the serosal side at the end of each experiment (Berni Canani R, et al. *WJG* 2006, 12:4710-4715).

Results

The addition of sodium butyrate to the luminal side of the human enterocytes induced a decrease in the short circuit current (ΔIsc=−0.8±0.2 μA/cm²) and in the potential difference, but did not alter tissue conductance. The maximum decrease in Isc was observed approximately 35 minutes after addition of the substance. This variation in Isc was significantly different from that observed in control cells (p<0.001). The effect was dose-dependent with a maximum effect at the final concentration of 10 mM (FIG. 1).

Figure 2:
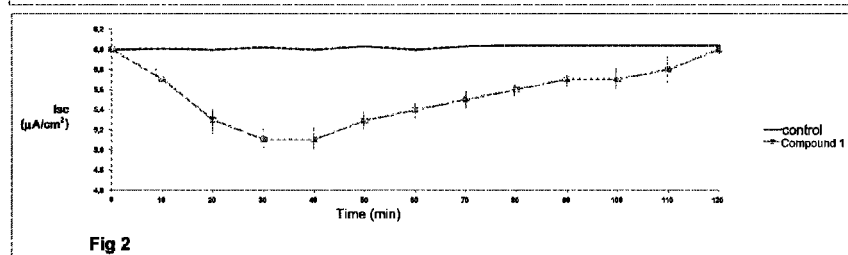

Similar experiments were done using the other compounds (compounds 1, 2 and 3). Compound 1 induced a dose-response decrease in Isc with a maximum effect at the final concentration of 10 mM (ΔIsc=−0.9±0.3 μA/cm²). The maximum decrease in Isc was observed approximately 40 minutes after addition to the mucosal side of the enterocytes, without interfering with the stability of tissue conductance. This variation in Isc was significantly different from that observed in control cells (p<0.001) (FIG. 2).

Figure 3:
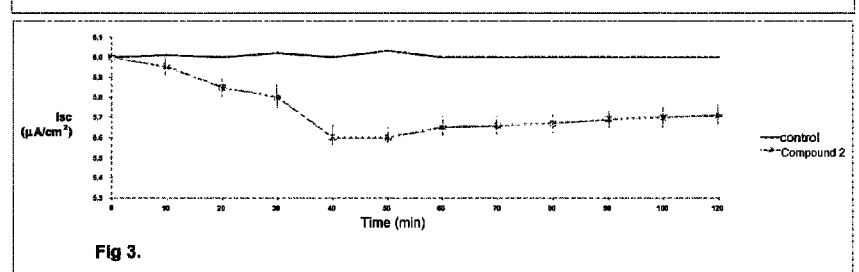

The addition of compound 2 to the luminal side of the enterocytes induced a dose-dependent decrease in Isc with a maximum effect at a concentration of 10 mM equal to −0.4±0.1 μA/cm². The maximum decrease in Isc was observed approximately 40-45 minutes after addition to the mucosal side of the enterocytes, without interfering with the stability of tissue conductance. This variation in Isc was significantly different from that observed in control cells (p<0.001). (FIG. 3).

Figure 4:
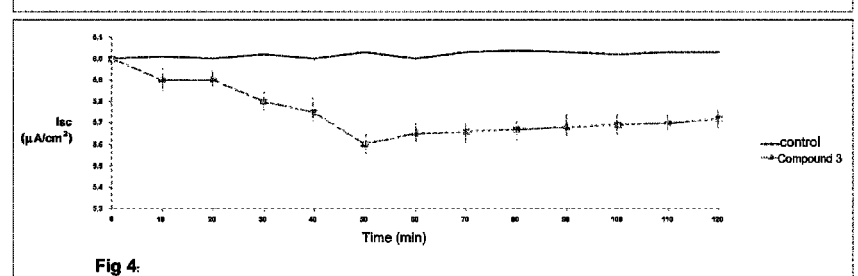

The addition of compound 3 to the luminal side of the enterocytes induced a dose-dependent decrease in Isc with a maximum effect at the final concentration of 10 mM equal to −1.1±0.1 μA/cm² in the absence of any significant changes in tissue conductance. The maximum peak effect was observed after a significantly longer time with respect to the other two compounds (40 min vs 50 min, p<0.001). This decrease in Isc was significantly greater than the one observed in control cells (p<0.001). (FIG. 4).

Figure 5:
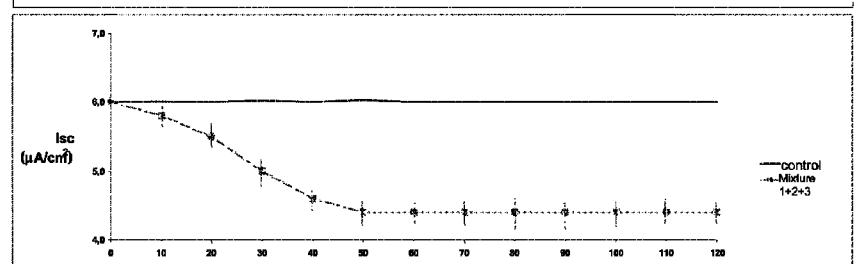

Addition to the luminal side of human enterocytes in culture of a 60/20/20% mixture of compounds 1, 2 and 3 equivalent to 10 mM of sodium butyrate induced a significantly more marked decrease (p<0.001) as compared to that observed with sodium butyrate 10 mM alone or with compounds 1, 2 and 3 with a maximum effect at the final concentration of 10 mM equal to −1.6±0.2 μA/cm², without any effect on tissue conductance (FIG. 5).

To investigate whether the electrical effects observed were due to a net absorption of chloride (Cl⁻), experiments were carried out in the absence of Cl⁻ in the buffer. In this experimental condition equimolar concentrations of SO₄— were substituted for Cl⁻. In these conditions, addition of the compounds alone or in mixtures did not induce any changes in the electrical parameters, showing that the decrease in Isc was entirely due to the active transport of Cl⁻. The administration of CT (6×10⁻⁸ M) to the luminal side of the cellular monolayer, mounted in an Ussing chamber, induced an increase in Isc. This secretory effect was significantly reduced by preincubation of the cells with the mixture of compounds administered to the luminal side at a final concentration of 10 mM (+4.1±0.5 vs. +1.1±0.2 μA/cm², p<0.001). The in-vitro data currently available show that:

compounds 1, 2 and 3 tested singly, by direct interaction with the human enterocytes in culture, induce a net pro-absorptive effect on fluid transport at the intestinal level at the dose of 10 mM. The effect became maximal after approximately 25-55 minutes without any interference on tissue integrity. These effects are similar to that obtained with sodium butyrate. The mixture of compounds 1, 2 and 3 in the proportion used in the reaction mixture (60/20/20%) equivalent to 10 mM of sodium butyrate, via a direct interaction with human enterocytes in culture, induced a net pro-absorptive effect on fluid transport at intestinal level. The effect became maximal 45 minutes after addition and remained stable until the end of the experiment without any interference with tissue integrity. This effect is similar kinetically with that obtained with the single compounds, but is significantly more intense and prolonged over time compared to that obtained with the single components. A potent antisecretory effect on cholera toxin, the prototypical of a secretory agent at the intestinal level, was also demonstrated The present invention has been described with reference to a number of its specific embodiments, but it should be understood that variations or modifications can be made by experts in the field without, for this reason, departing from its scope of protection.

The invention claimed is:

1. A compound obtainable by reaction of a butyroyl halide with a phenylalanine derivative according to a scheme, wherein the compound has the following formula:

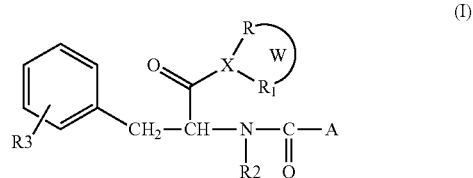

wherein

Y represents an atom of halogen, alkoxyl (2-6 carbon atoms), acyl (2-6 carbon atoms);

A represents:
(i) a branched $C_{(1-5)}$ alkyl chain, or a branched $C_{(1-5)}$ alkyl chain substituted with a phenyl,
(ii) a straight $C_{(1-5)}$ alkyl chain substituted with phenyl, or,
(iii) a straight $C_{(1-5)}$ alkyl chain wherein A is not a methyl group;

X represents nitrogen,

R and $R_1$ independently represent, hydrogen or a $(C_{1-6})$ alkyl group or a $(C_{1-6})$ acyl group and W is nil; or W represents a 1,2-alkylene chain with 2 to 6 carbon atoms and R and $R_1$ are methylene groups;

$R_2$ and $R_4$ independently represent, hydrogen or a $(C_{1-6})$ alkyl group or a $(C_{1-6})$ acyl group; and $R_3$ is selected from the group consisting of H, $(C_{1-6})$alkyl, $(C_{1-6})$ alkoxyl, halogen, oxidryl, cyano, nitro, amino, mono- or di-$(C_{1-6})$alkylamino, $(C_{2-6})$acylamino, formyl, hydroxyiminomethyl, $(C_{1-6})$alkoxyiminomethyl and carbamoyl; or a salt thereof, or a diastereoisomeric form thereof, or an enantiomeric form thereof, or a mixture thereof, and wherein the scheme comprises:

reacting a short-chain fatty acid derivative with a phenylalanine derivative according to the following scheme:

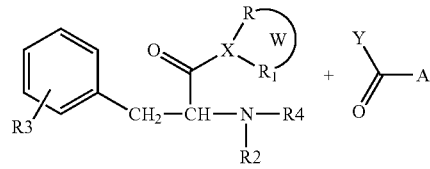

wherein:
  Y represents an atom of halogen, alkoxyl (2-6 carbon atoms), acyl (2-6 carbon atoms);
  A represents:
    (i) a branched $C_{(1-5)}$ alkyl chain, or a branched $C_{(1-5)}$ alkyl chain substituted with a phenyl,
    (ii) a straight $C_{(1-5)}$ alkyl chain substituted with phenyl, or,
    (iii) a straight $C_{(1-5)}$ alkyl chain wherein A is not a methyl group;
  X represents nitrogen,
  R and $R_1$ independently represent, hydrogen or a $(C_{1-6})$ alkyl group or a $(C_{1-6})$ acyl group and W is nil; or
  W represents a 1,2-alkylene chain with 2 to 6 carbon atoms and R and $R_1$ are methylene groups;
  $R_2$ and $R_4$ independently represent, hydrogen or a $(C_{1-6})$ alkyl group or a $(C_{1-6})$ acyl group;
  $R_3$ is selected from the group consisting of H, $(C_{1-6})$alkyl, $(C_{1-6})$ alkoxyl, halogen, oxidryl, cyano, nitro, amino, mono- or di-$(C_{1-6})$alkylamino, $(C_{2-6})$acylamino, formyl, hydroxyiminomethyl, $(C_{1-6})$alkoxyiminomethyl and carbamoyl, or a salt thereof, or a diastereoisomeric form thereof, or an enantiomeric form thereof, or a mixture thereof.

2. A compound selected from the group consisting of:
(a)
N-(1-carbamoyl-2-phenyl-ethyl)butyramide;
N-(1-butyroyl-carbamoyl-2-phenyl-ethyl)butyramide;
5-benzyl-2-propyl-1H-imidazol-4(5H)-one;
N-(1-carbamoyl-p-toluyl-methyl)butyramide;
N-(2-carbamoyl-1-phenylethyl)butyramide;
N-(4(2-carbamoylethyl)phenyl)butyramide;
N-(1-oxo-3-phenyl-1-(piperidin-1-yl)propan-2-yl)butyramide;
N-(1-oxo-3-phenyl-1-(pyrrolidin-1-yl)propan-2-yl)butyramide;
N-(1-(methylcarbamoyl)-2-phenylethyl)butyramide;
N-(1-(ethylcarbamoyl)-2-phenylethyl)butyramide;
N-(1-(propylcarbamoyl)-2-phenylethyl)butyramide;
N-(1-(butylcarbamoyl)-2-phenylethyl)butyramide;
N-(1-(pentylcarbamoyl)-2-phenylethyl)butyramide;
N-(1-carbamoyl-2-phenylethyl)-N-methylbutyramide;
N-(1-carbamoyl-2-phenylethyl)-N-ethylbutyramide; or
N-(1-carbamoyl-2-phenylethyl)-N-propylbutyramide;
and
a salt thereof, or a diastereoisomeric form thereof, or an enantiomeric form thereof, or a mixture thereof.

3. A mixture of amide derivatives of butyric acid according to claim 2, consisting essentially of the following three compounds:
N-(1-carbamoyl-2-phenyl-ethyl)butyramide, with formula:

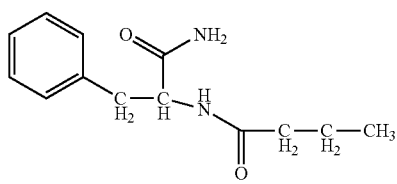 [SMILES: CCCC(=O)NC(Cc1ccccc1)C(N)=O]

N-(1-butyroyl-carbamoyl-2-phenyl-ethyl)butyramide, with formula:

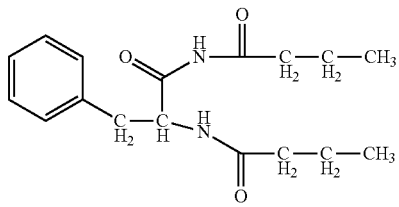 [SMILES: CCCC(=O)NC(=O)C(Cc1ccccc1)NC(=O)CCC]

5-benzyl-2-propyl-1H-imidazol-4(5H)-one, with formula:

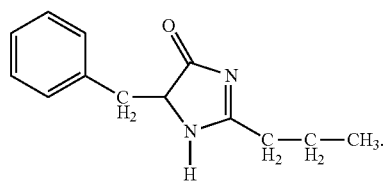 [SMILES: CCCC1=NC(=O)C(Cc2ccccc2)N1]

4. A compound of claim 1, formulated as a medical or a veterinary pharmaceutical or a dietary composition.

5. A pharmaceutical or a dietary composition comprising an active ingredient comprising a compound of claim 1.

6. The pharmaceutical or dietary composition of claim 5:
  (a) further comprising one or more pharmacologically acceptable adjuvants and/or vehicles, or
  (b) in combination with or formulated with a dietary supplement, a functional food, a nutraceutical or a medical device.

7. The pharmaceutical or dietary composition of claim 5 formulated for human nutrition or animal nutrition.

8. The pharmaceutical or dietary composition of claim 5, formulated for oral, topical or parenteral administration.

9. The compound of claim 1, further comprising a pharmaceutically acceptable base or acid thereof.

10. The compound of claim 1, wherein the diastereoisomeric form or the enantiomeric form comprises a pure diastereoisomeric form or a pure enantiomeric form.

11. The compound of claim 2, further comprising a pharmaceutically acceptable base or acid thereof.

12. The compound of claim 2, wherein the diastereoisomeric form or the enantiomeric form comprises a pure diastereoisomeric form or a pure enantiomeric form.

13. The compound of claim 1, wherein $A=CH_2CH_2CH_3$.

14. The compound of claim 1, wherein $R_2$ and $R_3$ represent hydrogen and R represents hydrogen or a methyl group.

15. The compound of claim 1, wherein $A=CH_2CH_2CH_3$, X represents a nitrogen, $R_1$ represents hydrogen, $R_2$ and $R_3$ represent hydrogen and R represents hydrogen or a methyl group.

16. A compound of claim 2, formulated as a medical or a veterinary pharmaceutical or a dietary composition.

17. A pharmaceutical or a dietary composition comprising an active ingredient comprising a compound of claim 2.

18. The pharmaceutical or dietary composition of claim 16, further comprising one or more pharmacologically acceptable adjuvants and/or vehicles.

19. The pharmaceutical or dietary composition of claim 16, in combination with or formulated with a dietary supplement, a functional food, a nutraceutical or a medical device.

20. The compound of claim 1, wherein A represents a branched $C_{(1-5)}$ alkyl chain, or a branched $C_{(1-5)}$ alkyl chain substituted with a phenyl.

21. The compound of claim 1, wherein A represents a straight $C_{(1-5)}$ alkyl chain substituted with phenyl.

22. The compound of claim 1, wherein A represents a straight $C_{(1-5)}$ alkyl chain and A is not a methyl group.

23. The compound of claim 1, wherein R represents hydrogen or a $(C_{1-6})$ alkyl group, and $R_1$ and W are nil.

* * * * *